US011523836B2

(12) United States Patent
Jacka et al.

(10) Patent No.: US 11,523,836 B2
(45) Date of Patent: Dec. 13, 2022

(54) SURGICAL GUIDE SYSTEM

(71) Applicant: 360 Hip Systems Pty Limited, New South Wales (AU)

(72) Inventors: William Jacka, New South Wales (AU); Dean Luke Pinchen, New South Wales (AU); Brad Peter Miles, New South Wales (AU); Peter Bede O'Connor, New South Wales (AU)

(73) Assignee: 360 HIP SYSTEMS PTY LIMITED, New South Wales (AU)

( * ) Notice: Subject to any disclaimer, the term of this patent is extended or adjusted under 35 U.S.C. 154(b) by 175 days.

(21) Appl. No.: 16/997,330

(22) Filed: Aug. 19, 2020

(65) Prior Publication Data

US 2021/0052290 A1 Feb. 25, 2021

(30) Foreign Application Priority Data

Aug. 20, 2019 (AU) ................................ 2019903034

(51) Int. Cl.
*A61B 17/17* (2006.01)
*A61B 17/84* (2006.01)
*A61B 17/56* (2006.01)
*A61B 17/00* (2006.01)

(52) U.S. Cl.
CPC ......... *A61B 17/1742* (2013.01); *A61B 17/84* (2013.01); *A61B 2017/00526* (2013.01); *A61B 2017/564* (2013.01)

(58) Field of Classification Search
CPC ............ A61B 17/1742; A61B 17/1746; A61B 17/175; A61B 17/1753; A61B 17/15; A61B 17/155; A61B 17/1739; A61B 17/151; A61B 17/152
See application file for complete search history.

(56) References Cited

U.S. PATENT DOCUMENTS

2017/0112628 A1* 4/2017 Dressler ............. A61B 17/1668

* cited by examiner

*Primary Examiner* — Samuel S Hanna
(74) *Attorney, Agent, or Firm* — Kilpatrick Townsend & Stockton LLP

(57) ABSTRACT

A surgical guide system for guiding a surgical tool, comprising a body which comprises a first contact surface profiled to locate with a first anatomical surface of a first bone; and a second contact surface profiled to locate with a second anatomical surface of a second bone; wherein the body is configured, for a specified functional position of the first bone relative to the second bone, to simultaneously: locate the first contact surface with the first anatomical surface; locate the second contact surface with the second anatomical surface; and receive, or guide, a first fastener to fasten to the first bone, wherein at least one of the body and/or the first fastener forms a first reference to guide a first surgical tool to the first bone.

7 Claims, 10 Drawing Sheets

SURGICAL GUIDE SYSTEM

CROSS REFERENCE TO RELATED APPLICATIONS

The present application claims priority from Australian Patent Application No. 2019903034 filed on Aug. 20, 2019, which is incorporated herein by reference in its entirety.

TECHNICAL FIELD

The present disclosure relates to a surgical guide system for guiding surgical tools.

BACKGROUND

It is important to accurately position surgical tools during surgery to allow the most effective treatment. One example includes orthopaedic surgery in relation to bones and joints, such as knee and hip replacement surgery. This may involve cutting, or otherwise shaping, bone and cartilage of the patient and securing implantable components thereto.

To assist accuracy a surgical guide may be placed relative to anatomic landmarks of the patient. Anatomic landmarks may include portions of the surface of the bone, cartilage and soft tissue constructs. The surgeon may then position surgical tools relative to the surgical guide. The surgical guide may then assist a blade to cut the bone, assist drilling into the bone, assist insertion of pins into the bone, and/or assist positioning and securing an implantable component to the bone.

A surgical guide may be configured (i.e. tailored) for a particular patient. For example, this may involve a CT scan (X-ray computed tomography) or MRI (magnetic resonance imaging) to determine anatomic landmarks of the bone, cartilage and/or soft tissue constructs of the patient. This information may then be used to determine a shape of a surgical guide that can be placed in contact with the bone and cartilage and have one "unique location" (relative to the bone). A surgical guide may then be manufactured for the surgery. The surgical guide may also have slot, apertures or other structural feature to which other surgical tools are indexed.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A surgical guide system comprises a body. The body comprises a first contact surface profiled to locate with a first anatomical surface of a first bone and a second contact surface profiled to locate with a second anatomical surface of a second bone. The body is configured, for a specified functional position of the first bone relative to the second bone, to simultaneously: locate the first contact surface with the first anatomical surface, locate the second contact surface with the second anatomical surface and receive, or guide, a first fastener to fasten to the first bone. At least one of the body and/or the first fastener forms a first reference to guide a first surgical tool to the first bone.

The surgical guide system may further comprise a first fastener guide portion selectively located to receive the first fastener relative to the body and to guide the first fastener to the first bone.

The body of the surgical guide system may be configured to simultaneously locate the second contact surface with the second anatomical surface and receive, or guide, a second fastener to the second bone. At least one of the body and/or the second fastener may form a second reference to guide a second surgical tool.

The surgical guide system may further comprise a second fastener guide portion selectively located to receive the second fastener relative to the body and to guide the second fastener to the second bone.

The body of the surgical guide system may comprise a first body portion with the first contact surface and a second body portion with the second contact surface. In a first configuration of the body, the first body portion is attached to second body portion to receive, or guide, the first fastener to the first bone. In a second configuration of the body, the first body portion and second body portion are selectively detached from one another.

The first body portion may be fastened to the first bone with the first fastener, and the first body portion may further comprise a first interface to receive the first surgical tool.

The second body portion may be fastened to the second bone with the second fastener and the second body portion may further comprise a second interface to receive the second surgical tool.

The body of the surgical guide system may be monolithic and have the first contact surface and second contact surface in a specified, and fixed, geometric relationship with one another. The body may further comprise one or more interfaces to receive a first surgical tool.

The surgical guide system may further comprise the first fastener fastened to the first bone, and the body is selectively separable from the first fastener and the first bone. The first fastener may be the first reference for the first surgical tool.

The first bone may be a bone forming at least part of the acetabulum, and the second bone may be a femur.

A method of installing a surgical guide, wherein a surgical guide system comprises a body with a first contact surface and a second contact surface, wherein the first contact surface and second contact surface are in a specified geometric relationship and profiled to correspond to a first anatomical surface of a first bone and a second anatomical surface of a second bone at a specified functional position. The method comprises locating the second contact surface with the second anatomical surface, locating the first contact surface with the first anatomical surface by moving the second bone relative to the first bone to the specified functional position. While the first and second contact surfaces are located with corresponding first and second anatomical surfaces, the method further comprises fastening a first fastener to the first bone wherein the first fastener is received, or guided, with the body, and indexing a first surgical tool to at least one of the body and/or the first fastener that forms a first reference to guide the first surgical tool to the first bone.

The method may, before the step of fastening the first fastener to the first bone, further comprise fastening the body to the second bone with a second fastener.

The method may further comprise indexing a second surgical tool to at least one of the body and/or the second fastener that forms a second reference to guide the second surgical tool to the second bone.

Where the surgical guide system includes one or more first fastener guide portions located relative to the body, the step of fastening the first fastener may comprise guiding the first fastener to the first bone with the first fastener guide portion.

Where the surgical guide system includes one or more second fastener guide portions located relative to the body, the step of fastening the second fastener may comprise guiding the second fastener to the second bone with the second fastener guide portion.

The method, wherein the body may comprise a first body portion with the first contact surface and a second body portion with the second contact surface, wherein in a first configuration of the body the first body portion is attached to the second body portion and in a second configuration of the body the first body portion and the second body portion are detached, wherein the body is in the first configuration during the steps of locating the first contact surface with the first anatomical surface and fastening the first fastener to the first bone; and wherein the method may comprise, subsequent to the step of fastening the first fastener to the first bone, the step of selectively detaching the first body portion from the second body portion to the second configuration.

Where the first portion may comprise a first interface to receive the first surgical tool, and wherein after the step of selectively detaching the first body portion from the second body portion, the first body portion may be fastened to the first bone with the first fastener, and the method may further comprise interfacing the first surgical tool to the first interface.

Where the second portion comprises a second interface to receive the second surgical tool, and wherein after the step of selectively detaching the first body portion from the second body portion, the second body portion may be fastened to the second bone with the second fastener, and the method may further comprise interfacing the second surgical tool to the second interface.

After the step of fastening the first fastener to the first bone, the method may further comprise selectively separating the body from the first fastener and the first bone, wherein the step of indexing the first surgical tool comprises indexing the first surgical tool to the first fastener.

The method, wherein the body may be monolithic and wherein the body may further comprise one or more interfaces to receive a first surgical tool.

The method wherein the first bone is a bone forming at least part of the acetabulum, and the second bone is the femur.

A method of manufacturing a surgical guide system comprising receiving, from a medical imaging device, imaging data of at least part of a first bone and a second bone of a patient while the patient is in a specified functional position, determining based on imaging data, a first anatomical surface of the first bone and the second anatomical surface of the second bone in the specified functional position, determining, based on the determined first and second anatomical surfaces in the specified functional position, an exterior profile of a body of a guide system and exporting a representation of the exterior profile of the body to be manufactured. The exterior profile comprises a first contact surface to locate with the corresponding first anatomical surface and a second contact surface to locate with the corresponding second anatomical surface. The first contact surface and second contact surface are on the exterior profile in a specified geometric relationship, and wherein simultaneously and uniquely locating the first and second contact surfaces with corresponding first and second anatomical surfaces correspond to the first and second bones to be in the specified functional position.

The method may further comprise the step of manufacturing the body with the exterior profile for the patient.

The method may further comprise determining one or more first references located relative to the body and exporting spatial data indicative of the relative position of the first reference(s) with the first bone.

The method may further comprise determining a location of a first fastener guide portion at the body. The first fastener guide portion receives a first fastener to guide the first fastener to the first bone, and the first fastener guide portion and/or the first fastener is at least part of the first reference.

BRIEF DESCRIPTION OF DRAWINGS

Examples of the present disclosure will be described with reference to.

DESCRIPTION OF EMBODIMENTS

Overview

Figure 1:
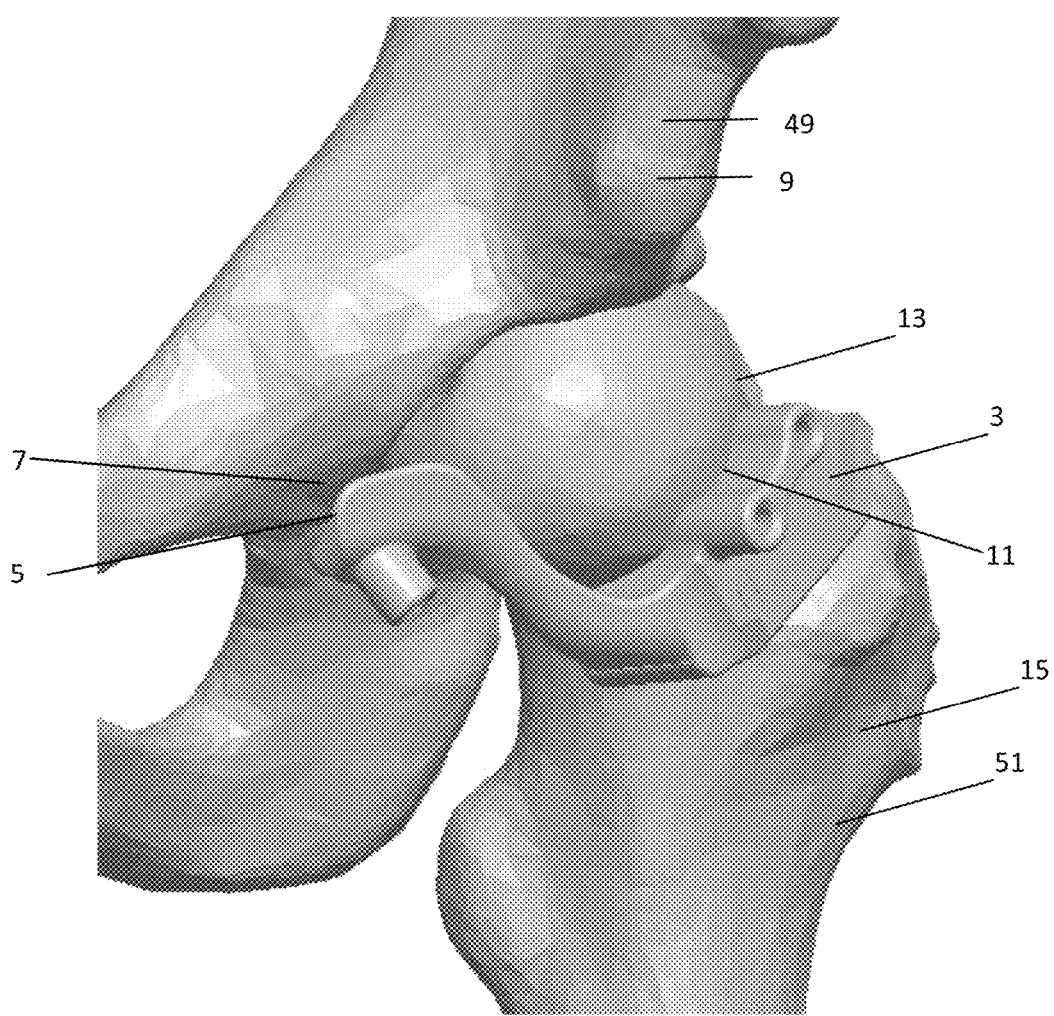
FIG. 1 illustrates a perspective view of a surgical guide system for a first bone and second bone.

FIG. 1 illustrates a surgical guide system 1 for guiding a surgical tool. The surgical guide system includes a body 3 that has a first and second contact surface 5, 11 profiled to locate with a first and second anatomical surface 7, 13 of a first and second bone 9, 15 respectively. The body 3 is configured, for a specified functional position 17 of the first bone 9 relative to the second bone 15, to simultaneously locate the first contact surface 5 with the first anatomical surface 7 and locate the second contact surface 11 with the second anatomical surface 13. In other words, the first contact surface 5 and second contact surface 11 are in a specified geometric relationship and profiled to correspond to a first anatomical surface 7 of a first bone 9 and a second anatomical surface 13 of a second bone 15 at a specified functional position 17. The body 3 is also configured to receive, or guide, a first fastener 23 to fasten to the first bone 9 so that at least one of the body 3 and/or the first fastener 23 forms a reference 25 to guide a surgical tool 27 to the first bone 9.

The placement of the body 3 is dependent on the orientation of the first bone 9 relative to the second bone 15 for the specified functional position 17. This allows the user, such as a surgeon, to be assured that the reference 25 has been positioned at a desired position on the first bone 9 relative to the second bone 15. During surgery, a surgeon may then refer to reference 25 to accurately determine the position and/or orientation of surgical tools to allow the most effective treatment.

The surgical guide system 1 may have application for a variety of orthopaedic surgeries. This may include procedures related to bone, cartilage and/or soft tissue constructs. Some specific applications include, but are not limited to, preparation for joint replacement surgery (such as hip, knee and elbow).

Figure 3:
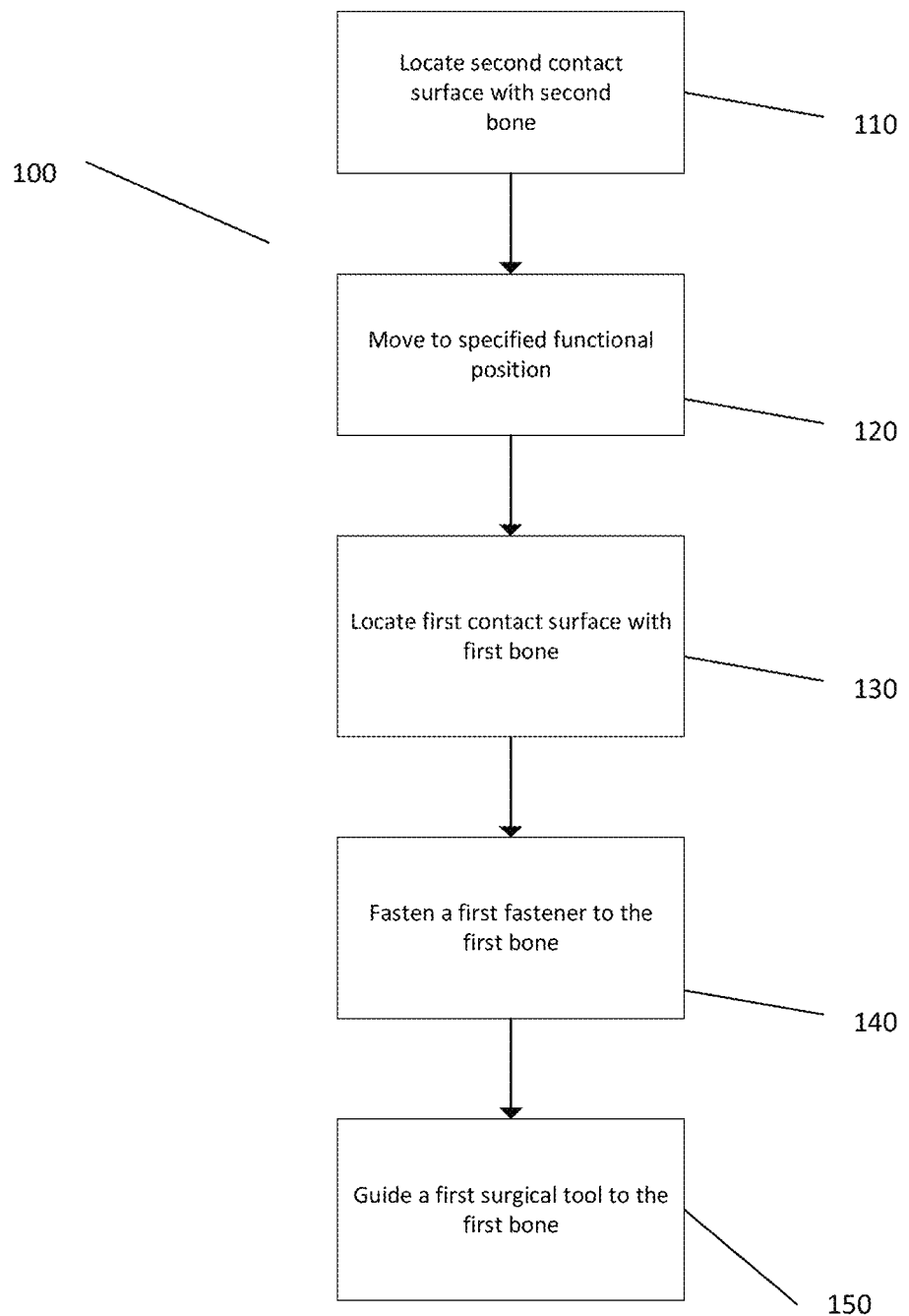
FIG. 3 is a flow chart illustrating a method for installing the surgical guide system of FIG. 1.

FIG. 3 is a flow chart illustrating a method 100 of installing the surgical guide system 1. A user, such as a surgeon, performs method 100 to install the surgical guide system 1 on the first bone 9 and second bone 15. Standard preoperative steps known to the person skilled in the art such as sterilisation are omitted from the description of method 100 and subsequent methods described herein.

Before performing method 100, the surgeon may perform the necessary procedures to expose the first bone 9 and/or second bone 15. At step 110, the user locates the second contact surface 11 with the second anatomical surface 13 of the second bone 15. The user the positions the patient at step 120 into a specified posture to functionally align the first bone 9 relative to the second bone 15 into the specified functional position 17. At step 130, the user subsequently locates the first contact surface 5 with the first anatomical surface 7 such that the first and second contact surfaces 5, 11 are simultaneously located with corresponding first and second anatomical surfaces 7, 13. The user then fastens a first fastener 23 to the first bone 9 at step 140 wherein the first fastener 23 is received, or guided, with the body 3. At step 150, the user indexes a first surgical tool 27 to at least one of the body 3 and/or the first fastener 23 that forms a first reference 25 to guide the first surgical tool 27 to the first bone 9.

In the preferred embodiment, the surgical guide system 1 is configured to contact the acetabulum 49 (also referred to as acetabulum 7) of the pelvis 9 at a first contact surface 5 and the head/neck 13 of the femur 51 (also referred to as femur 15) at a second contact surface 11 to guide a surgeon performing a full hip replacement surgery.

For the hip, prior surgical guides are used separately on the femur and pelvis. Existing femoral surgical guides are accurate and reliable at providing a reference at the correct placement to guide surgical tools. However, existing pelvic surgical guides are less accurate and reliable at providing a reference at the correct placement. The surgical guide system 1 takes advantage of the accuracy and reliability of existing femoral surgical guides to deliver an accurate and reliable placement of the pelvic or acetabulum reference 25.

Fabrication

An example of how the surgical guide system 1 may be fabricated will now be described.

Figure 2:
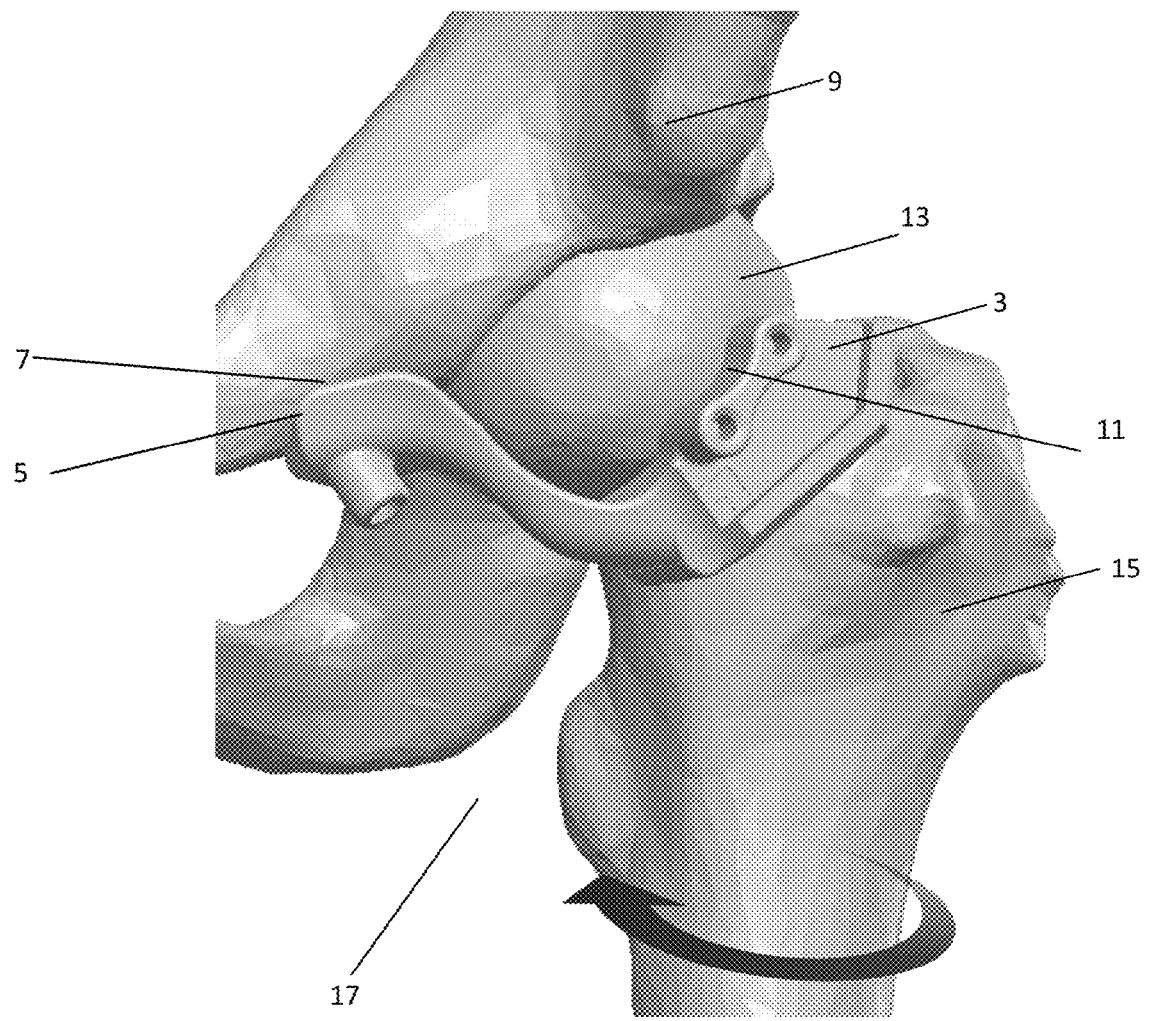
FIG. 2 illustrates a perspective view of a surgical guide system of FIG. 1 wherein the first bone and second bone is in a specified functional position.

Referring to FIG. 2, the surgical guide system 1 may be preoperatively manufactured specifically for a patient. Imaging data of at least part of a first bone 9 and a second bone 15 of the patient is collected non-invasively when the patient is positioned in a specified functional posture. When the patient is in the specified functional posture, the first bone 9, relative to the second bone 15 is in a specified functional position 17. A first anatomical surface 7 and second anatomical surface 13 of the first bone 9 and second bone 15 respectively in the specified functional position 17 is determined based on the imaging data.

The patient's geometry of the determined first and second anatomical surface 7, 13 in the specified functional position 17 is then used to determine an exterior profile 61 of the body 3 of the surgical guide system 1 to form a patient specific design. The exterior profile 61 includes a first contact surface 5 and second contact surface 11 to locate with the corresponding first anatomical surface 7 and second anatomical surface 13 respectively.

The first contact surface 5 and second contact surface 11 are on the exterior profile 61 in a specified geometric relationship, wherein simultaneously locating the first and second contact surfaces 5, 11 with corresponding first and second anatomical surfaces 7, 13 uniquely corresponds to the first and second bones 9, 15 of the specific patient being in the specified functional position 17.

A representation of the exterior profile of the body 3 may be exported to manufacture the body 3.

Figure 4:
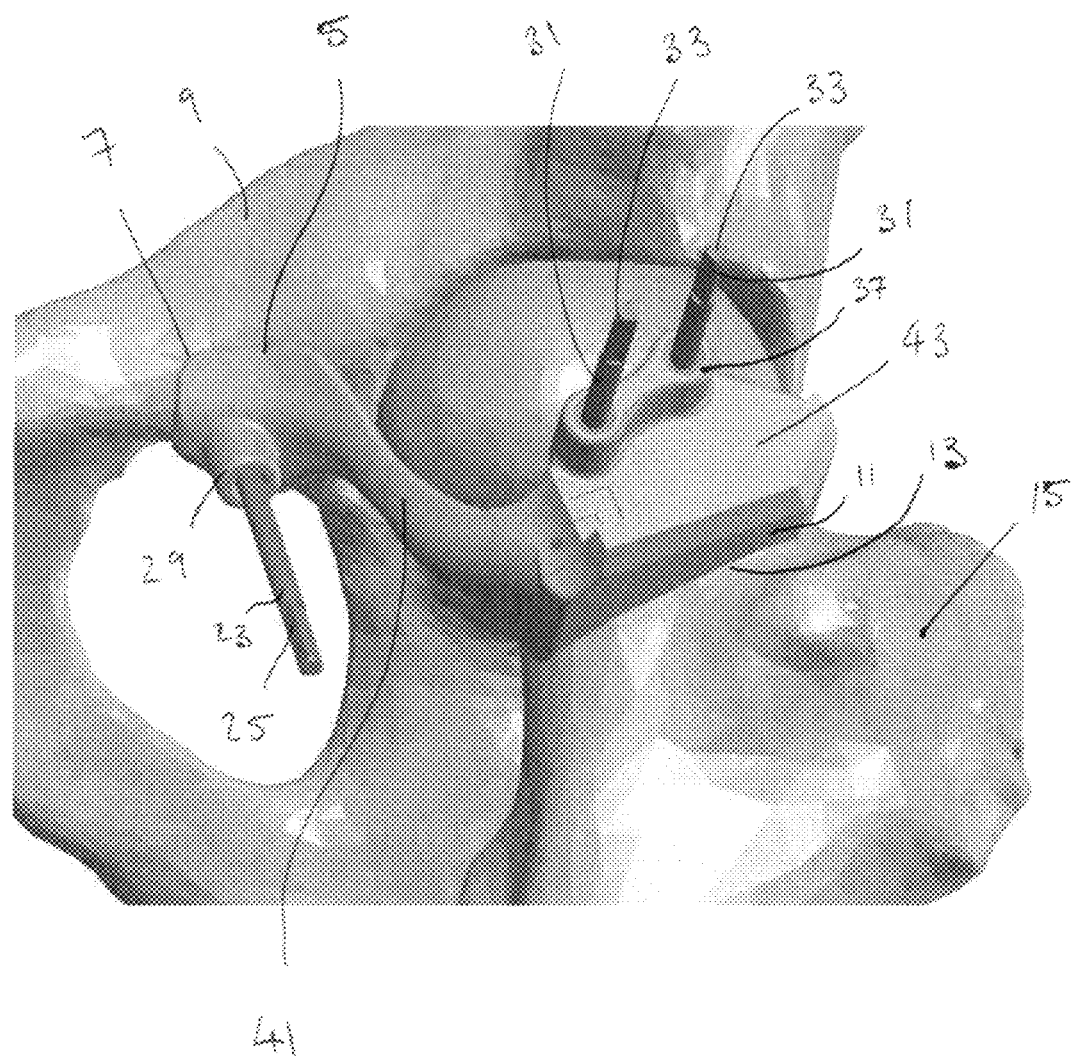
FIG. 4 illustrates a perspective view of an embodiment of the surgical guide system of FIG. 1 with fasteners attached.

Referring now to FIG. 4, spatial data of the one or more first references 25 (also referred to individually as first reference 25) located relative to, or part of the body 3 may be determined, which is indicative of the relative position of the first reference(s) 25 with the first bone 9. This data may be exported for manufacturing so that the first reference(s) is correctly positioned to index a first surgical tool 27 to the first bone 9 when the body 3 is simultaneously located with the first and second bones 9, 15 in the specified functional position 17.

Where the body 3 includes a first and/or second fastener guide portion 29, 37, the location of the first and/or second fastener guide portions 29, 37 at the body 3 is determined for manufacturing. A detailed description of the first and second fastener guide portions 29, 37 is provided below.

In one form, additive or subtractive manufacturing techniques may be used to manufacture the body 3 in accordance with the representation 63 of the exterior profile 61 of the body 3. In one example, the body 3 may be manufactured from 3D printing technology, such as using selective laser sintering to produce a body of polyamide (nylon). In another example, the body 3 may be manufactured with a CNC milling process. Further examples may include a combination of additive and subtractive manufacturing techniques as well as other manufacturing techniques (such as injection moulding). These processes may be advantageous by providing tailored parts for the particular patient in a cost effective manner.

Body of the Preferred Embodiment

The features of the preferred embodiment of the body 3 of the surgical guide system 1 will now be described in a non-limiting example with references to FIGS. 1, 2, 4, 5 and 6. In the preferred embodiment, the surgical guide system 1 is directed to assisting surgeons guide surgical tools during a hip replacement operation. In the following description of the preferred embodiment, the first anatomical surface 7 of the first bone 9 refers to the acetabulum 7 of the pelvis 9 and the second anatomical surface 13 of the second bone 15 refers to the head/neck 13 (also referred to as head 13) of the femur 15.

In FIG. 1, the first anatomical surface 7 of the first bone 9 is not in a specified functional position relative to the second anatomical surface 13 of the second bone 15. The body 3 of the surgical guide system 1 is positioned such that the second contact surface 11 is located on the second anatomical surface 13 of the second bone 15, and the first contact surface 5 is not located on the first anatomical surface 7 of the first bone 9.

FIG. 2 depicts where the first anatomical surface 7 of the first bone 9 is in a specified functional position 17 relative to the second anatomical surface 13 of the second bone 15. In the specified functional position 17, the body 3 of the surgical guide system 1 is configured to simultaneously locate the first contact surface 5 with the first anatomical surface 7 and the second contact surface 11 with the second anatomical surface 13.

The specified functional position 17 of the first bone 9 relative to the second bone 15 may be patient specific, and may be determined from a specified posture of the patient. The surgeon is able to position the patient, who may be sedated, into the specified posture to position the first bone 9 relative to the second bone 15 in a specified functional position 17.

The first and second contact surfaces 5, 11 of the body 3 may be profiled to correspond closely to the first and second anatomical surface 7, 13 of the first and second bone 9, 15 of a specific patient, such that a surgeon may be able to more easily locate the first and second contact surface 5, 11 onto the first and second anatomical surfaces 7, 13.

Referring now to FIG. 4, the body 3 in the specified functional position 17 is configured to receive, or guide, one or more first fasteners 23 (also referred to individually as first fastener 23) to fasten at least first fastener 23 to the first bone 9. Once the first fastener 23 is fastened or affixed to the first bone 9, the first fastener 23 forms a first reference 25 to guide a first surgical tool 27 to the first bone 9. In some examples, the first fastener 23 is a first surgical pin configured to at least partially penetrate through the body 3 and affix itself to the first bone 9. Subsequent to fastening the first fastener 23 to the first bone 9, the body may be configured to separate from the first fastener 23 and the first bone 9, leaving the first fastener 23 affixed to the first bone 9 as a first reference 25.

During a hip replacement surgery, a surgeon delivers an acetabular cup implant on the acetabulum 7 of the pelvis 9 (as the first bone 9) with a first surgical tool 27 which is configured to be guided by the one or more affixed first surgical pins 23 (also referred to individually as first surgical pin 23) as the first reference 25.

The first surgical tool 27 may be an Acetabular Reamer Handle or an Acetabular Cup Impactor, such as those manufactured by Greatbatch. The Acetabular Reamer Handle, which aligns a hemispherical reamer to prepare the surface of the pelvis (as the first bone) 9 to accept the acetabular cup implant, is guided by holding the shaft of the reamer handle parallel to the first reference 25. The Acetabular Cup Impactor, which connects to the acetabular cup implant for final impaction and delivery of the implant, is similarly guided by holding the shaft of the Acetabular Cup Impactor parallel to the first reference 25.

The body 3 may also comprise a first fastener guide portion 29 which is selectively located on the body 3 to receive and guide the first fastener 23 to the first bone 9. The first fastener guide portion 29 may be proximate to the first contact surface 5, and include an aperture or hole that extends at least partially through the body 3 to receive and precisely guide the first fastener 23 (such as the first surgical pin 23) through the first contact surface 5 to the first bone 9 to fasten at least one of the first fastener 23 and/or body 3 to the first bone 9. As seen in FIG. 4, the first fastener guide portion 29 may also protrude from the body 3, which enables a surgeon to easily locate and guide the first fastener 23 through the aperture of the first fastener guide portion 29.

Referring still to FIG. 4, subsequent to locating the second contact surface 11 with the second anatomical surface 13 of the second bone 15, the body 3 may also be configured to receive, or guide one or more second fasteners 31 (also referred to individually as second fastener 31) to fasten at least the second fastener 31 the second bone 15. Once the second fastener 31 is fastened or affixed to the second bone 15, the second fastener 31 forms a second reference 33 to guide a second surgical tool 35 to the second bone 15. In some examples, the second fastener 31 is a second surgical pin 31 configured to penetrate at least partially through the body 3 and affix itself to the femur (as the second bone) 15. Subsequent to fastening the second fastener 31 to the second bone 15, the body may be configured to separate from the second fastener 31 and the second bone 15, leaving the second fastener 31 affixed to the second bone 15 as a second reference 33.

During a hip replacement surgery, a surgeon performs a femoral neck resection on the head 13 of the femur 15 (as the second bone 15) with a second surgical tool 35 configured to be guided by one or more affixed second surgical pins 31 (also referred to individually as second surgical pin 31) as second reference(s) 33. The second surgical tool 35 may be an orthopaedic saw to perform a femoral neck resection. In some examples, the orthopaedic saw is guided by a guide placed over references 33.

The body 3 further comprises a second fastener guide portion 37 which is selectively located on the body 3 to receive and guide the second fastener 31 to the second bone 15. In the preferred embodiment, the second fastener guide portion 37 may be proximate to the second contact surface 11, and includes an aperture that extends at least partially through the body 3 to receive and precisely guide the second fastener 31 (such as a second surgical pin 31) through the second contact surface 11 to the second bone 15 to fasten at least one of the second fastener 31 and/or body 3 to the second bone 15. Similarly, the second fastener guide portion 37 may also protrude from the body 3, to enable a surgeon to more easily locate and guide the second fastener 31 through the aperture of the second guide portion 37.

Figure 5:
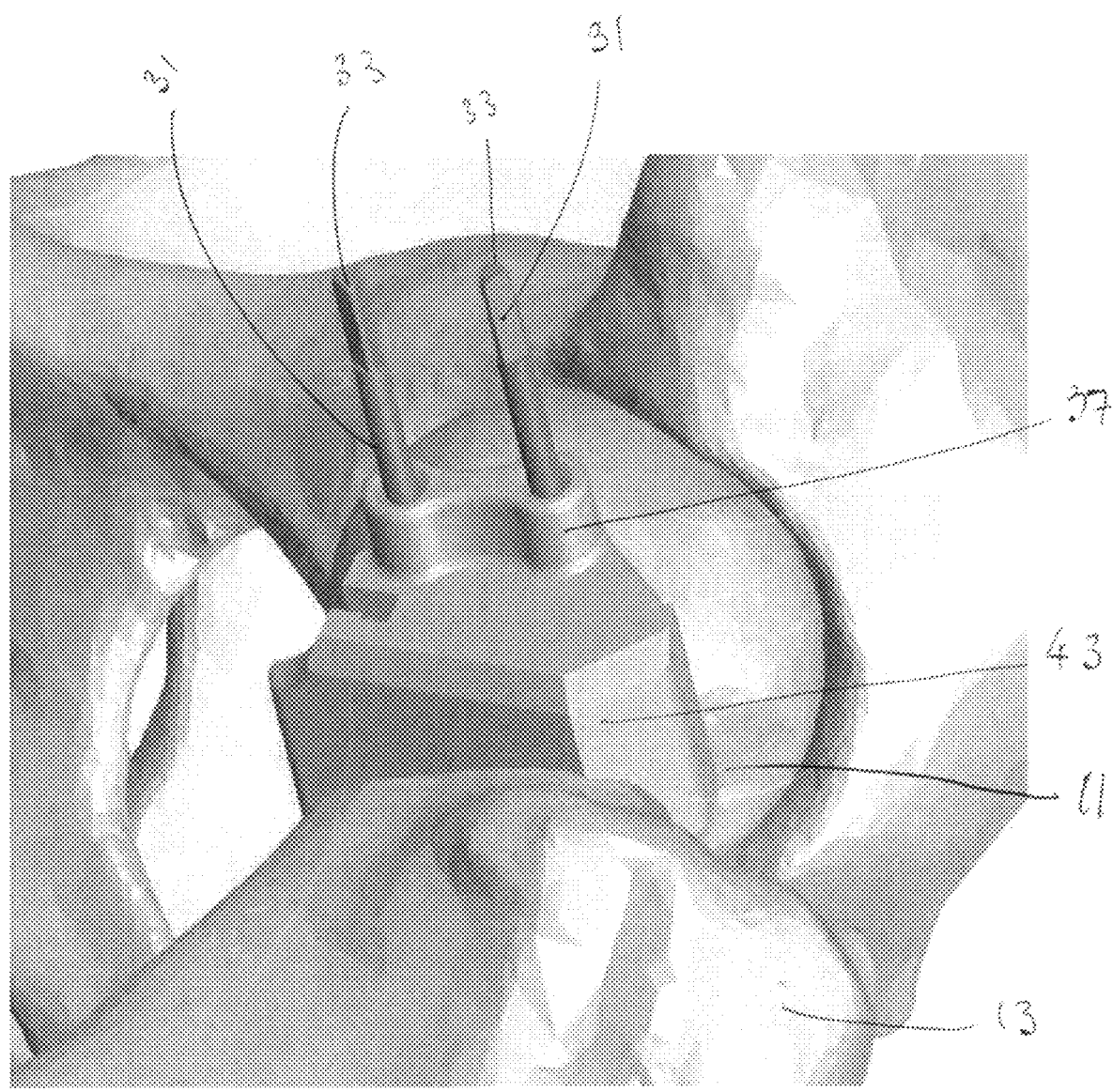
FIG. 5 illustrates a perspective view of the first body portion of the surgical guide system of FIG. 4.
Figures 6A, 6B:
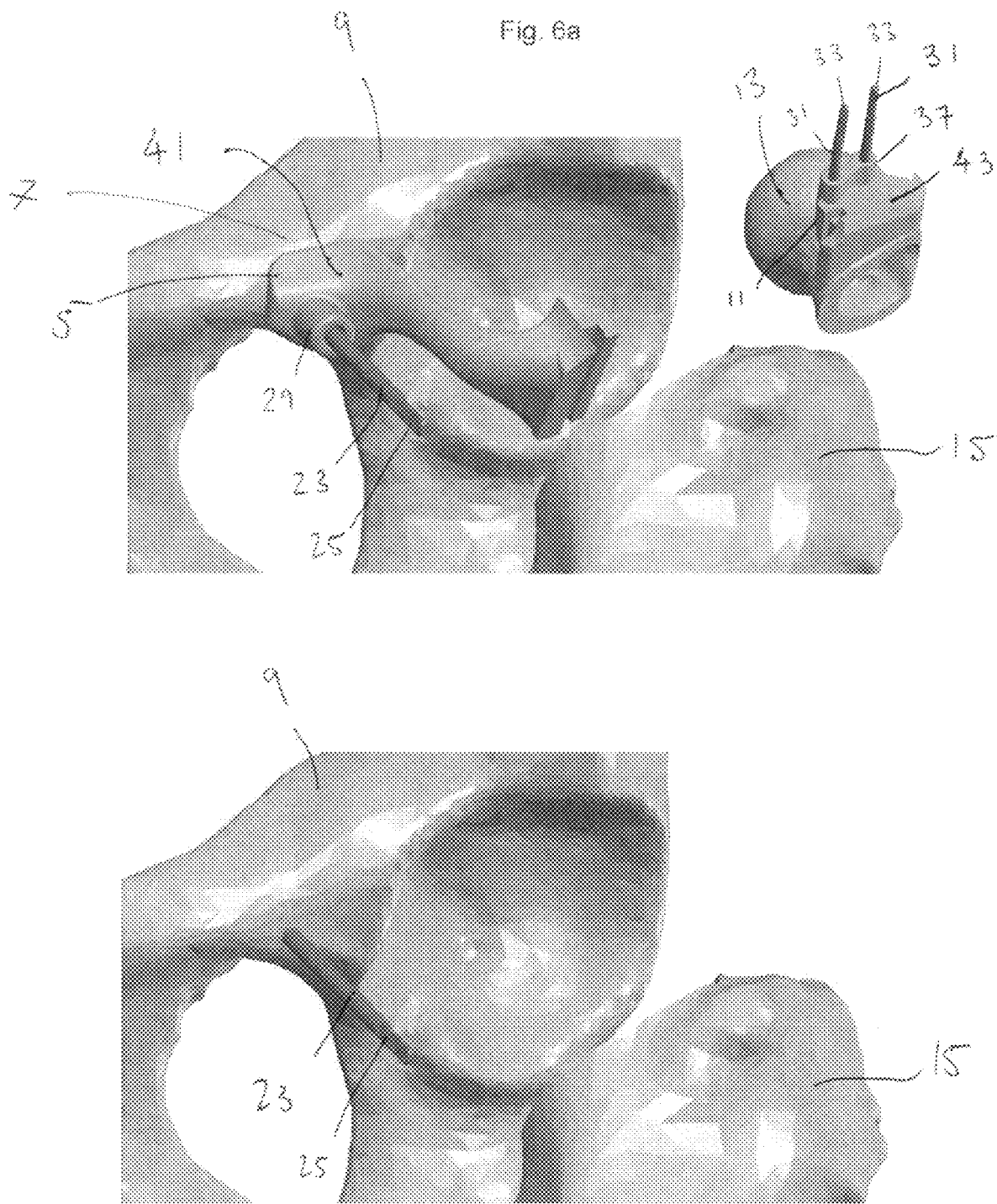
FIG. 6a illustrates a perspective view of the surgical guide system where the first and second body portions are separable.
FIG. 6b illustrates a perspective view of the surgical guide system where the body is removed from the first fastener.

Referring now to FIGS. 5 and 6a, the body 3 may comprise a first body portion 41 with the first contact surface 5, and a second body portion 43 with the second contact surface 11. In this embodiment, the body 3 is a two-piece body, where the first body portion 41 may be selectively detachable from the second body portion 43. The first configuration of the body 3 is where the first body portion 41 is attached to the second body portion 43 (as shown in FIG. 4). FIG. 6a illustrates the second configuration of the body 3, wherein the first body portion 41 and second body portion 43 are selectively detached from one another.

The patient specific profile 61 of the body 3 is configured to simultaneously contact the first and second bone 9, 15 if and only if the first and second bone 9, 15 are in the specified functional position 17. Hence, a surgeon must maintain the patient in the specified posture corresponding to the specified functional position 17 once the body 3 is affixed to the first and second bone 9, 15. A modular, two-piece body 3 is able to selectively detach the first body portion 41 from the second body portion 43. This advantageously allows the surgeon to adjust the position of the first and second bone 9, 15 away from the specified functional position 17, by detaching the two body portions 41, 43 once the first and second fastener 23, 31 are fastened to corresponding first bone 9 and second bone 15.

Referring now to FIG. 6b, once the first fastener 23 is fastened to the first bone 9, the first body portion 41 (or the body 3) can be selectively separable from the first fastener 23 and the first bone 9. As such, the first body portion 41 (or body 3) may be removed from the first bone 9, leaving the first fastener 23 fastened to the first bone 9 to form a first reference 25 to guide a first surgical tool 27 to the first bone 9. By detaching the first body portion 41 (or body 3) from the first fastener 23, the surgeon is able to guide the first surgical tool 27 to the first bone 9 without the body 3 or first body portion 41 potentially restricting the range of motion of the first surgical tool 27. The body 3 may be selectively detached from the first fastener 23 after the second fastener 31 is fastened to the second bone 15.

Once the second fastener 31 is fastened to the second bone 15, in some embodiments the second body portion 43 (or body 3) can also be selectively separable from the second fastener 31 and the second bone 15. As such, the body 3 may be removed from the second fastener 31 and second bone 15, leaving the second fastener 31 fastened to the second bone 15 to form a second reference 33 to guide a second surgical tool 35 to the second bone 15. Detaching the body 3 from the second fastener 31 may allow the surgeon to operate without restricting range of motion of the second surgical tool 35.

Figure 7:
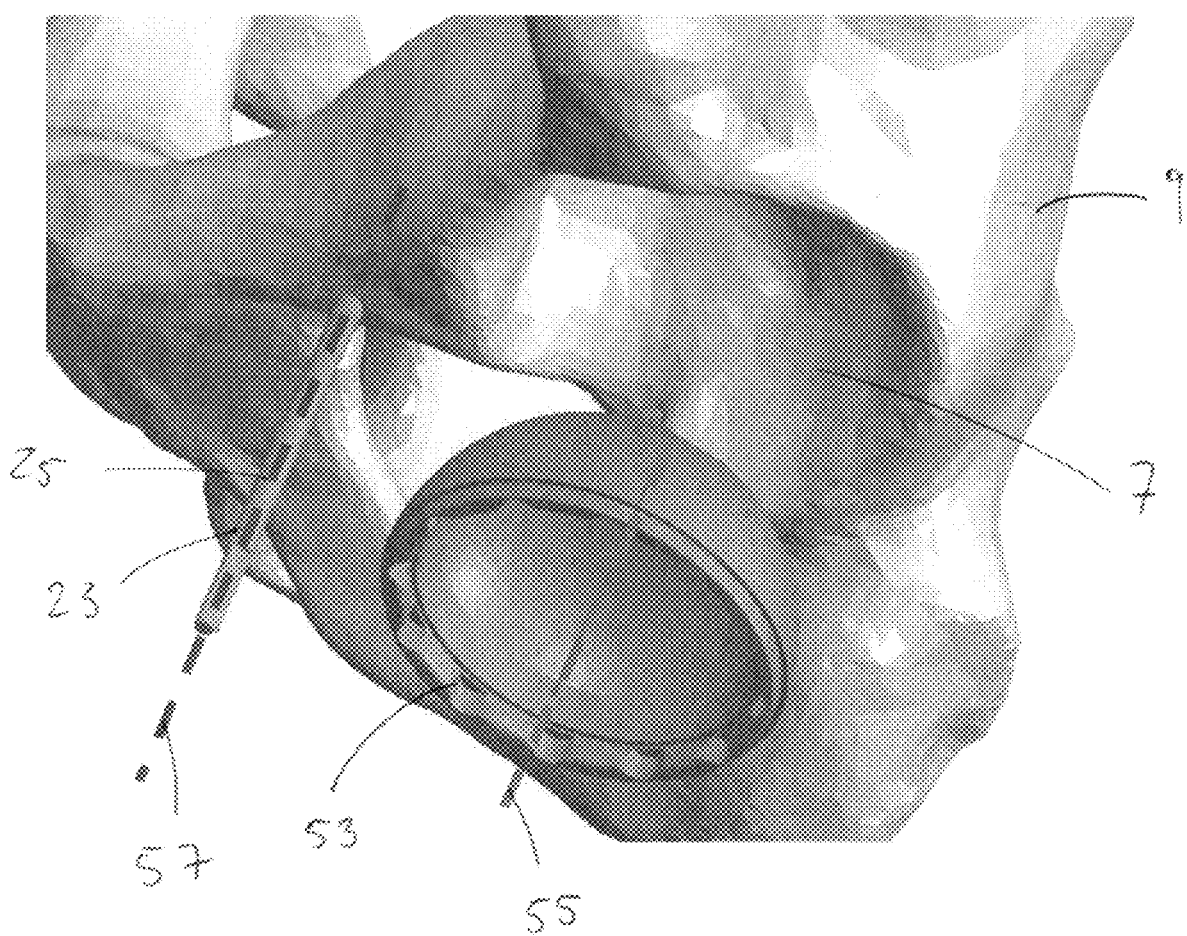
FIG. 7 illustrates a perspective view of the surgical guide system where the first fastener forms a first reference for installing an acetabulum cup implant.

Referring now to FIG. 7, during a hip replacement surgery the surgeon implants an acetabular cup 53 into the acetabulum 7 of the pelvis 9. The placement and alignment plane 55 of the acetabular cup influences the range of motion of the leg and also affects the risk of dislocation. Accordingly, the first fastener 23 (or first surgical pin 23) is advantageously aligned to a preoperatively planned alignment plane 57 for the acetabular cup implant. As the Acetabular Reamer Handle and Acetabular Cup Impactor are guided by holding the shaft parallel to the first reference 25 and hence the first fastener 23, the acetabular cup is delivered to the acetabulum in alignment with the preoperatively planned alignment plane 57.

Method of Installing the Preferred Embodiment

An example of how the preferred embodiment of surgical guide system 1 may be installed by a user, such as a surgeon, will now be described with reference to FIGS. 1, 4, 5, 6, 7 and 8.

Figure 8:
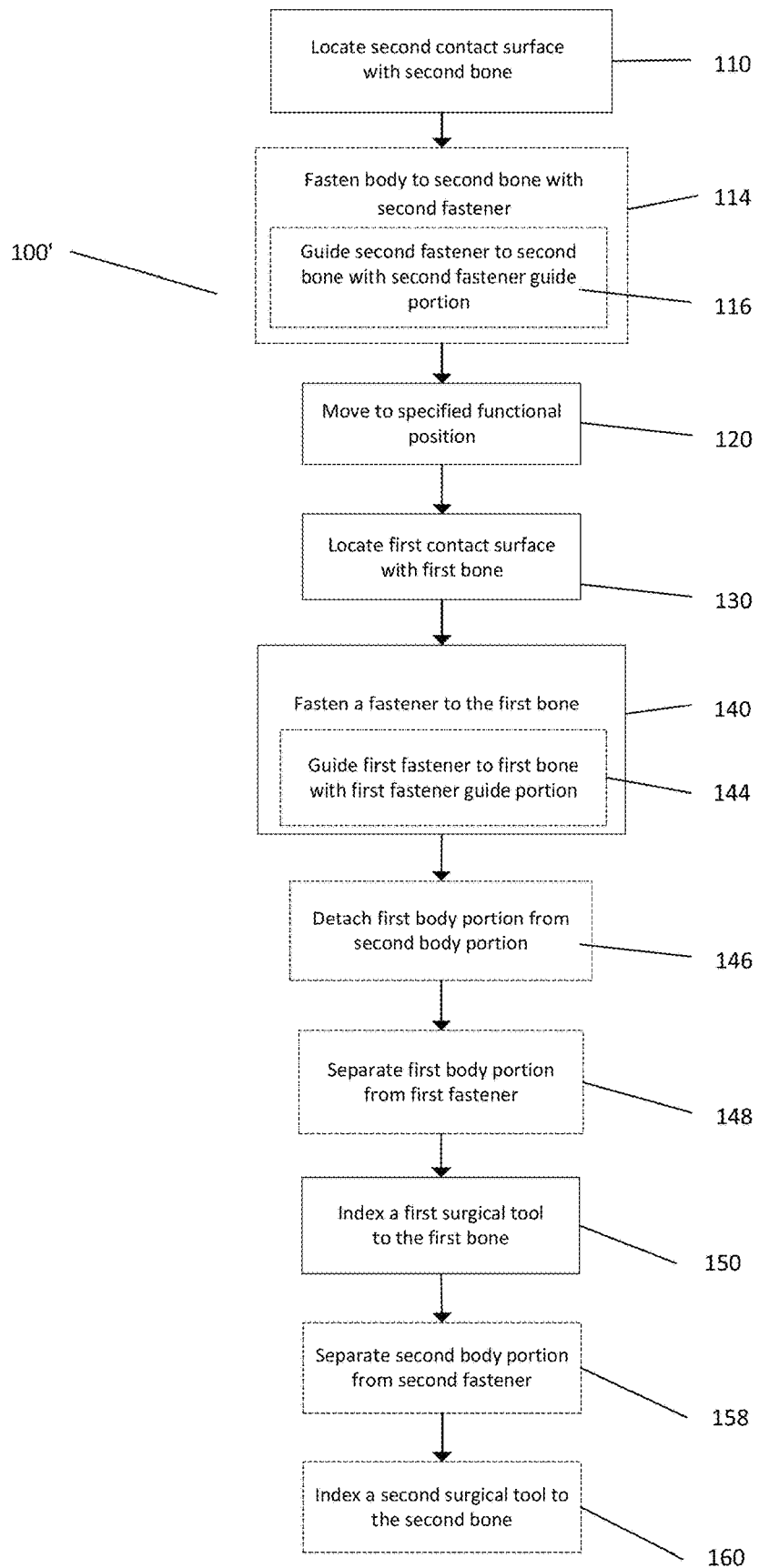
FIG. 8 is a flow chart illustrating a method for installing the surgical guide system of FIG. 5.

FIG. 8 is a flow chart illustrating a method 100' of installing the surgical guide system 1 of FIG. 5. Method 100' expands on method 100 of FIG. 3, and the steps of method 100' are a superset of the steps of method 100. Steps in common have been given identical references. Further steps are depicted as dashed line rectangles, and specific variants of broader steps are depicted as nested rectangles. Before performing method 100', the surgeon may perform the necessary procedures to expose the first bone 9 and/or second bone 15.

As depicted in FIG. 1, at step 110, a surgeon locates the second contact surface 11 with the second anatomical surface 13 of the second bone 15. As depicted in FIG. 5, the surgeon subsequently fastens, at step 114, the body 3 to the second bone 15 with the second fastener 31 by guiding, at step 116, the second fastener 31 to the second bone 15 with the second fastener guide portion 37. By fastening the body 3 to the second bone 15 first, it is ensured that the body 3 is securely affixed so that it is easier to posture the patient to the specified functional position 17 without dislocating the body 3 from the second bone 15. Step 110 to 116 enables the surgeon to accurately position and affix the second contact of the body 3 onto the desired position onto the second anatomical surface 13 of the second bone 15.

The surgeon then positions the patient at step 120 into a specified posture to functionally align the first bone 9 relative to the second bone 15 into the specified functional position 17. Advantageously, as the body 3 is already affixed to the second bone 15, the surgeon need not manually maintain the body 3 correctly located on the second bone 15 as the first bone 9 is aligned relative to the second bone 15 into the specified functional position 17.

At step 130, the surgeon subsequently locates the first contact surface 5 with the first anatomical surface 7 such that the first and second contact surfaces 5, 11 are simultaneously located with corresponding first and second anatomical surfaces 7, 13. The surgeon is assured that the desired position of the body 3 is achieved once the body 3 is simultaneously located with both first and second bones 9, 15 in the specified functional position 17.

As depicted in FIG. 4, at step 140, the surgeon fastens a first fastener 23 to the first bone 9 by guiding, at step 144 the first fastener 23 to the first bone 9 with the first fastener guide portion 29. Once the first body portion 41 and second body portion 43 are fastened to the first and second bone 9, 15, at step 146, as depicted in FIG. 6a the surgeon selectively detaches the first body portion 41 from the second body portion 43. This may allow the surgeon to adjust the posture of the patient to position the first bone 9 and/or second bone 15 in a position other than the specified functional position 17. As depicted in FIG. 6b at step 148, the surgeon selectively separates the first body portion 41 from the first fastener 23 and the first bone 9, leaving behind the first fastener 23 affixed to the first bone 9. Removing the first body portion 41 from the first bone 9 provides more space, enabling the surgeon to more easily guide a first surgical tool(s) 27 to the first bone 9.

At step 150, the surgeon indexes a first surgical tool 27 to the first fastener 23 to form a first reference 25 to guide the first surgical tool 27 to the first bone 9. As described above, the first surgical tool 27 may include one or more interfaces to interface with the first fastener 23 to position the first surgical tool 27 to the desired position relative to the first bone 9.

At step 158, the surgeon may optionally separate the second body portion 43 from the second fastener 31, leaving the second fastener 31 affixed to the second bone 15. At step 160 the surgeon indexes a second surgical tool 35 to the second fastener 31 that forms a second reference 33 to guide the second surgical tool 35 to the second bone 15. Similarly, the second surgical tool 35 may include one or more interfaces to interface with the second fastener 31 to position the second surgical tool 35 to the desired position relative to the second bone 15.

It is to be appreciated that the order of steps presented in the examples above can be varied. Steps can be re-ordered, combined or broken into sub-steps. Certain steps or processes can be performed in parallel. For example, steps 114 and 116 of method 100' may be performed subsequent to step 130, where the surgeon may simultaneously locate the body 3 with first bone 9 and second bone 15 before the fastening step of 114 and 116.

Other Examples of a Surgical Guide System

It is to be appreciated that the description of the preferred embodiment with reference to FIGS. 1, 2 and 4 to 7 is non-limiting and that features, or combinations of features of the preferred embodiment may, in some potential examples, be omitted. Accordingly, a user, such as a surgeon, may perform a subset of steps of the method 100', but a superset of the steps of method 100 to install such embodiments of the surgical guide system 1.

In an example, the surgical guide system 1 of FIG. 4 may not comprise a first and/or second fastener guide portions 29, 37. In this example, the body 3 does not have specific holes or apertures and the body 3 instead configured to receive (and not guide) the first fastener 23 and/or second fastener 31 to fasten to the first bone 9 and/or second bone 15 as described in the overview. A surgeon may install the surgical guide system of this example by carrying out method 100' where step 114 and 144 are omitted. For example, a surgeon fastens the body 3 to the second bone 15 and/or first bone 9 by passing the fastener through the body 3 and into the bone. In this example, the precise location of the fastener may not be important.

In other examples, the first and/or second fastener guide portions 29, 37 of the body 3 may be in the form of markings, indentations and/or the contouring of body 3 to guide a fastener to the bone. The surgeon may visually inspect and use the markings to guide the fastener to a desired position on the bone. Alternatively or in addition, the body may be include contours and/or indentations to guide the fastener to the desired position on the bone. Where the first and/or second fastener guide portions 29, 37 do not include an aperture to guide the first and/or second fastener 23, 31, the fastener guide portion may simply comprise of a material configured to allow a fastener such as a surgical pin to easily penetrate through the body 3 to the respective bone.

Where the fastener is a surgical pin, fastening may be performed by penetrating the surgical pin through the body 3 into the bone. In other examples, the first and/or second fastener 23, 31, may be a screw, wire, jig or clamp. Accordingly, fastener guide portions may be configured specifically for certain types of fasteners, but not others. It is to be appreciated that the fastener guide portion may include any combination of features to guide the first and/or second fastener 23, 31 to the first and/or second bone 9, 15.

In other examples, the first body portion 41 and/or second body portion 43 of the body 3 are not separable from the first fastener 23 and/or second fastener 31. In this example, the surgeon indexes the first surgical tool 27 to at least one of the body 3 (which comprises the first body portion 41 and second body portion 43) or first fastener 23, which forms a first reference 25, to guide the first surgical tool 27 to the first bone 9. The surgeon may also index the second surgical tool 35 to at least one of the body 3 or second fastener 31 which forms a second reference, to guide the second surgical tool 35 to the second bone 15.

Further variations of the surgical guide system 1 will now be described in non-limiting examples. Features common to previously described embodiments have been given identical reference numbers and will not be described again.

Figure 9:
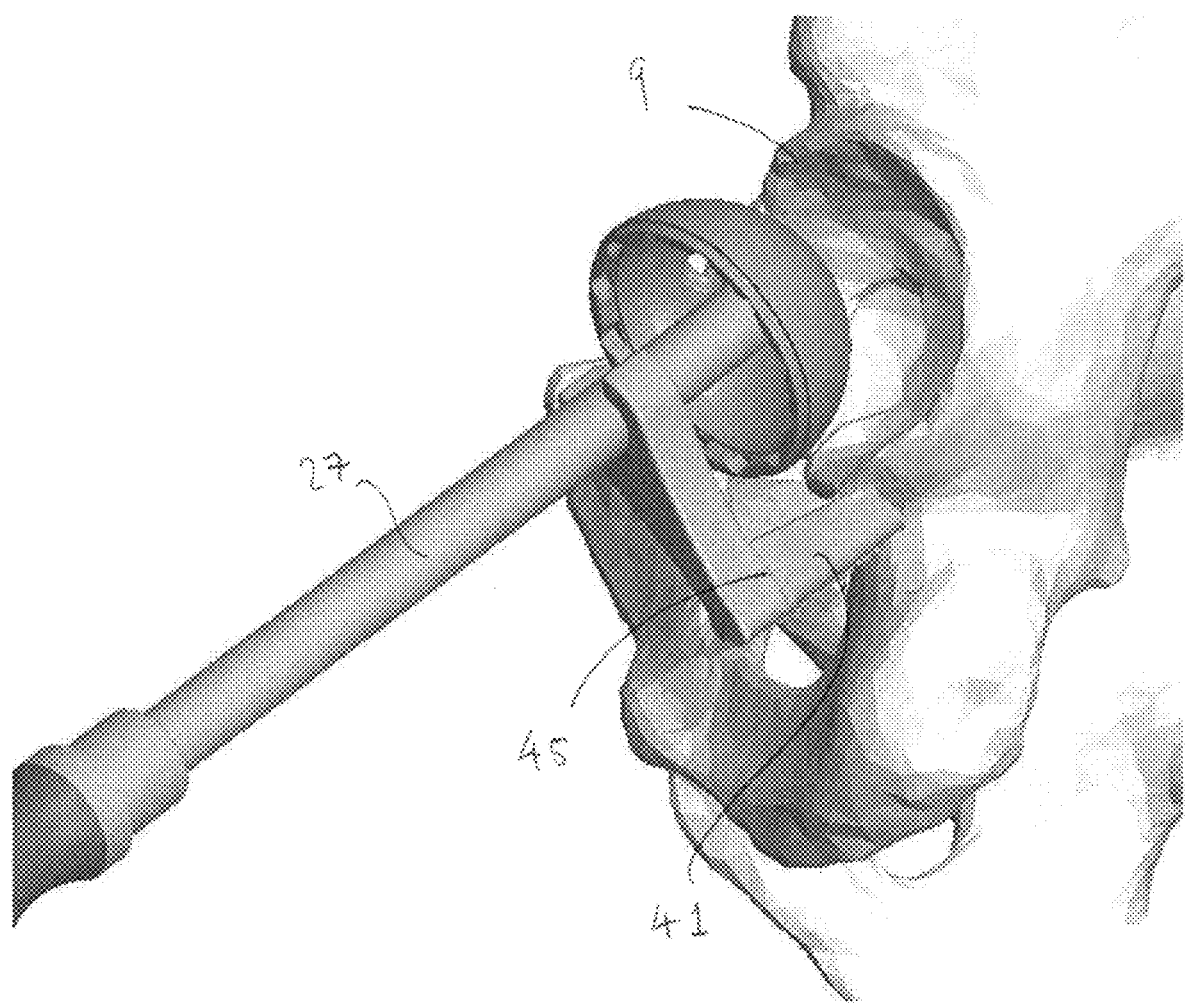
FIG. 9 illustrates a perspective view of another embodiment of the surgical guide system.

FIG. 9 illustrates another example of surgical guide system 1 for guiding a first surgical tool 27 to the first bone 9. The first body portion 41 is fastened to the first bone 9 with the first fastener 23 and further comprises a first interface 45 to receive the first surgical tool 27. The first interface 45 interfaces with the first surgical tool 27 to guide the surgical tool 27 to the first bone 9. As depicted in FIG. 9, the first surgical tool is an Acetabulum Impactor which connects to the acetabular cup implant for final impaction and delivery of the implant. The first interface may be for example, a socket, T-slot or threaded aperture (among other things) that interfaces with a corresponding interface of the first surgical tool 27. This arrangement supports and guides the first surgical tool 27 to the first bone 9.

Alternatively or in addition, the second body portion 43 of the surgical guide system 1 is fastened to the second bone 15 (with the second fastener 31), and may further comprise a second interface 47 to receive the second surgical tool 35. The second interface 47 interfaces with the second surgical tool 35 to guide the surgical tool 35 to the second bone. The second interface may also be for example, a socket, T-slot or threaded aperture (among other things) that interfaces with the second surgical tool 35, whereby the arrangement guides the second surgical tool 35 to the second bone 15.

In these examples, the body 3 itself, instead of the fastener, may form a first and/or second reference 25, 33 for the step of indexing 150 a first surgical tool 27 and indexing 160 a second surgical tool 35.

Figure 10:
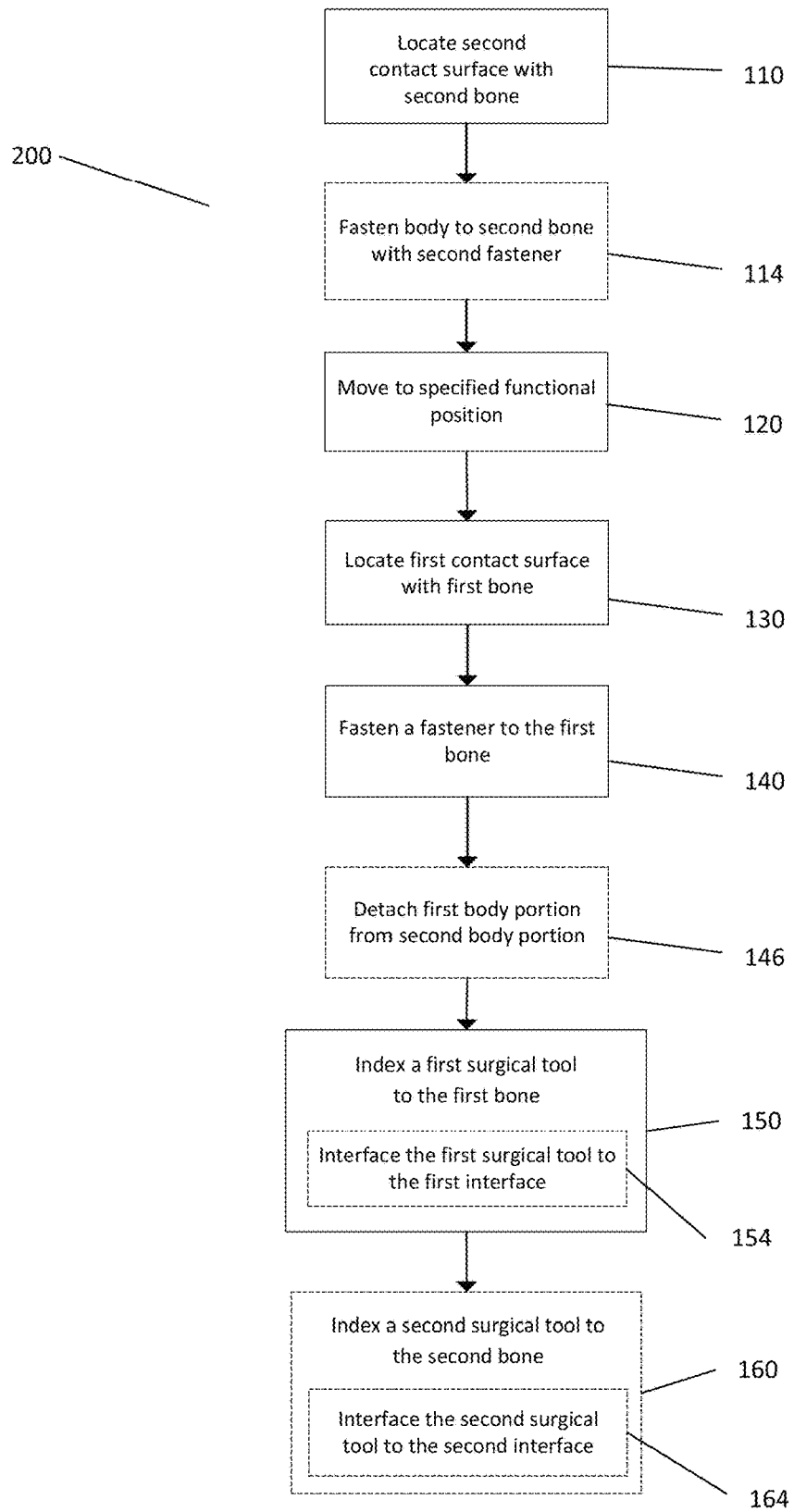
FIG. 10 is a flow chart illustrating a method for installing the surgical guide system of FIG. 9.

FIG. 10 illustrates a method 200 for installing the surgical guide system of FIG. 7. Steps in common are denoted identical reference numbers and will not be described again. Method 200 includes all the steps of method 100 in FIG. 3, with the addition of steps 114, 146, 154, 160 and 164. Step 114 and 146 are common with method 100' of FIG. 5. At step 150, the surgeon indexes a first surgical tool 27 to the first fastener by interfacing, at step 154, the first surgical tool 27 to the first interface 45 to guide the first surgical tool 27 to the first bone 9. At step 160, the surgeon indexes a second surgical tool 35 to the second fastener by interfacing, at step 164, the second surgical tool 35 to the second interface 47 to guide the second surgical tool 35 to the second bone 15.

In another example, the body 3 of the surgical guide system 1 is monolithic. The first contact surface 5 and second contact surface 11 is in a specified, and fixed, geometric relationship with one another. This means that the body is not a two-piece body where a first body portion is separable from a second body portion. As the body 3 is monolithic, the surgeon cannot detach, at step 146, the first body portion from the second body portion. Instead, the monolithic body 3 is separable from at least one of the first and second fasteners 23, 31, such that the surgeon can detach the monolithic body 3 from at least one of the first or second fastener 23, 31. The surgeon subsequently indexes a first surgical tool 27 and/or second surgical tool 35 with the first fastener 23 and/or second fastener 31 to guide the surgical tool to the bone.

The monolithic body 3 may further comprise one or more interfaces 45, 47 to receive a first surgical tool 27 and/or second surgical tool 35. The monolithic body 3 may also comprise a first fastener guide portion 29 and/or a second fastener guide portion 37, wherein the first and/or second fastener guide portions 29, 37 may take on any of the variations described above.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A surgical guide system comprising:
    a body comprising:
        a first contact surface profiled to locate with a first anatomical surface of a first bone, wherein the first bone forms at least part of an acetabulum, and wherein the first contact surface includes a first contouring surface that contacts the at least part of acetabulum; and a second contact surface profiled to locate with a second anatomical surface of a second bone, wherein the second bone forms at least part of a neck of a femur, and wherein the second contact surface includes a second contouring surface that contacts the at least part of the neck of the femur;

a first fastener guide portion selectively located to receive a first fastener through the body and to guide the first fastener into the first bone; and a second fastener guide portion selectively located to receive a second fastener through the body and to guide the second fastener into the second bone;

wherein the body is configured, for a specified functional position of the first bone relative to the second bone, to simultaneously:

locate the first contact surface with the first anatomical surface;

locate the second contact surface with the second anatomical surface;

receive, or guide, the first fastener to fasten the body to the first bone; and receive, or guide, the second fastener to fasten the body to the second bone, such that the body maintains the specified functional position of the first bone relative to the second bone; and wherein at least one of the body and/or the first fastener forms a first reference to guide a first surgical tool to the first bone.

2. The surgical guide system according claim 1, wherein at least one of the body and/or the second fastener forms a second reference to guide a second surgical tool.

3. The surgical guide system according claim 1, wherein the body comprises a first body portion with the first contact surface and a second body portion with the second contact surface, wherein in a first configuration of the body, the first body portion is attached to the second body portion to receive, or guide, the first fastener to the first bone, and wherein in a second configuration of the body, the first body portion and the second body portion are selectively detached from one another.

4. The surgical guide system according to claim 3, wherein the first body portion is configured to be fastened to the first bone with the first fastener, and wherein the first body portion further comprises a first interface to receive the first surgical tool.

5. The surgical guide system according to claim 3, wherein the second body portion is configured to be fastened to the second bone with the second fastener, and wherein the second body portion further comprises a second interface to receive a second surgical tool.

6. The surgical guide system according to claim 1, wherein the body is monolithic and has the first contact surface and the second contact surface in a specified, and fixed, geometric relationship with one another, and wherein the body further comprises one or more interfaces to receive the first surgical tool.

7. The surgical guide system according to claim 1, further comprising the first fastener is configured to be fastened to the first bone, and the body is selectively separable from the first fastener and the first bone, wherein the first fastener is the first reference for the first surgical tool.

* * * * *